United States Patent
Lin et al.

(12) 
(10) Patent No.: US 6,547,730 B1
(45) Date of Patent: Apr. 15, 2003

(54) ULTRASOUND INFORMATION PROCESSING SYSTEM

(75) Inventors: Shengtz Lin, Cupertino, CA (US); Zengpin Yu, Palo Alto, CA (US)

(73) Assignee: U-Systems, Inc., Los Altos, CA (US)

(*) Notice: Subject to any disclaimer, the term of this patent is extended or adjusted under 35 U.S.C. 154(b) by 0 days.

(21) Appl. No.: 09/224,635

(22) Filed: Dec. 31, 1998

(51) Int. Cl.[7] ............................................... A61B 8/00
(52) U.S. Cl. ...................................................... 600/437
(58) Field of Search .............................. 600/437, 407, 600/438, 440–447, 450–459, 463, 465; 128/903, 904; 382/128, 130, 131, 132; 341/65; 705/3; 395/705

(56) References Cited

U.S. PATENT DOCUMENTS

| | | |
|---|---|---|
| 4,853,875 A | 8/1989 | Brown |
| 5,295,485 A | 3/1994 | Shinomura et al. |
| 5,353,220 A | 10/1994 | Ito et al. |
| 5,483,963 A | 1/1996 | Butler et al. |
| 5,590,658 A | 1/1997 | Chiang et al. |
| 5,603,323 A | 2/1997 | Pflugrath et al. |
| 5,630,101 A | 5/1997 | Sieffert |
| 5,709,206 A | 1/1998 | Teboul |
| 5,715,823 A | 2/1998 | Wood et al. |
| 5,778,177 A | 7/1998 | Azar |
| 5,795,297 A | 8/1998 | Daigle |
| 5,838,592 A | 11/1998 | Spratt |
| 5,851,186 A | 12/1998 | Wood et al. |
| 5,853,367 A | 12/1998 | Chalek et al. |
| 5,891,035 A * | 4/1999 | Wood et al. ................. 600/437 |
| 5,971,923 A * | 10/1999 | Finger ......................... 600/437 |
| 5,997,478 A | 12/1999 | Jackson et al. |
| 6,101,407 A | 8/2000 | Groezinger |
| 6,241,673 B1 * | 6/2001 | Williams ...................... 600/437 |

* cited by examiner

Primary Examiner—Marvin M. Lateef
Assistant Examiner—Ali M. Imam
(74) Attorney, Agent, or Firm—Cooper & Dunham LLP (57) ABSTRACT

An architecture and protocol are provided for allowing flexible, low cost, and upgradable ultrasound information processing systems. Ultrasound information processing functions are performed by a plurality of ultrasound modules coupled to a high-speed, multiple-drop serial ultrasound information bus. The ultrasound information bus is used for packetized data transfer among the ultrasound modules in accordance with an ultrasound information exchange protocol. Additional or upgraded ultrasound modules are designed to connect to the ultrasound information bus and to communicate using the ultrasound information exchange protocol. Thus, according to a preferred embodiment, as improvements in hardware technology or software algorithms are made, additional or upgraded ultrasound modules are simply "plugged in" to the ultrasound information bus, hereby reducing costs and increasing system versatility and upgradability.

19 Claims, 8 Drawing Sheets

ULTRASOUND INFORMATION PROCESSING SYSTEM

FIELD OF THE INVENTION

The present invention relates to the field of ultrasound information processing systems. In particular, the present invention relates to an architecture and protocol for providing flexible, high performance, reduced cost, and readily upgradable ultrasound information processing systems.

BACKGROUND OF THE INVENTION

Medical imaging systems based on ultrasound technology are useful in that they are non-invasive and generally easy to use. An ultrasound imaging system transmits sound waves of very high frequency (e.g., 2 MHz to 10 MHz) into a patient and processes the echoes reflected from structures in the patient's body to form two dimensional or three-dimensional images. Depending on the system used and diagnostic needs of the patient, the ultrasound images are displayed in real-time or stored for archival or future diagnostics purposes.

Many ultrasound information processing algorithms are known in the art, e.g. echo mode ("B mode") processing algorithms, Doppler shift echo processing algorithms, color flow mode processing algorithms, and others. A common characteristic among the various ultrasound algorithms is a high degree of computational intensity and the need for high power, high speed hardware systems for performing the computationally intensive algorithms. Generally speaking, the implementation of higher performance ultrasound information processing leads to the desirable results of greater image resolution and/or frame rate for given ultrasound algorithm.

Figure 1:
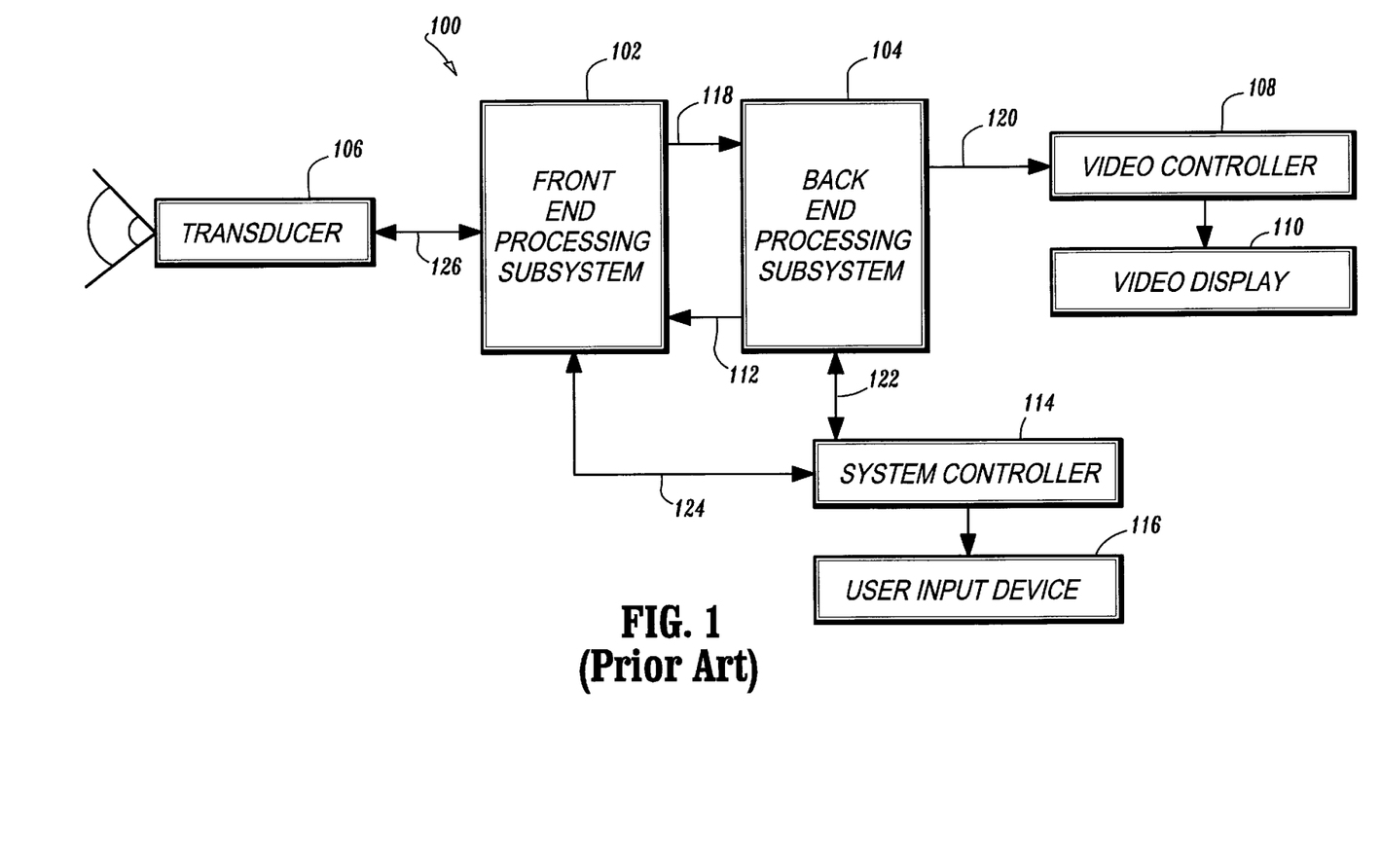
FIG. 1 shows an ultrasound information processing system in accordance with a prior art architecture.

FIG. 1 shows an ultrasound information processing system 100 in accordance with a prior art architecture. The ultrasound information processing system 100 is similar in several respects to a system disclosed in U.S. Pat. No. 5,709,209, "Ultrasound Signal Processing System," the contents of which are hereby incorporated by reference into the present disclosure. Ultrasound information processing system 100 comprises a front end processing subsystem 102, a back end processing subsystem 104, a transducer 106, a video controller 108, a video display 110, a system controller 114, and a user input device 116.

Transducer 106 sends acoustical signals toward a subject, the acoustical signals being formed in accordance with electrical scan signals. Front end processing subsystem 102 produces the electrical scan signals based on scan parameters, receives echo signals from the subject responsive to the acoustical signals, and produces multidimensional vector data associated with the echo signals. Back end processing subsystem 104 receives and processes the multidimensional vector data to produce image data and parameter information, and provides the parameter information back to the front end processing subsystem 102. Processing of the multidimensional vector data by back end processing subsystem 104 includes, for example, echo signal processing, color flow processing, or Doppler processing. Video controller 108 and video display 110 are used to display the image data. Finally, system controller 114 and user input device 116 are used for controlling the overall functions of the system and for receiving user input, respectively.

The architecture of the ultrasound information processing system 100 contains limitations that reduce its flexibility, versatility, and upgradability. In particular, the architecture comprises a series of custom, dedicated communications links among the transducer 106, the processing subsystems 102 and 104, the system controller 114, and the video units 108 and 110. These include the links 112, 118, 120, 122, 124, and 126 in FIG. 1.

The link 118, for example, is dedicated in that it represents a communications path only between the front end processor 102 and the back end processor 104. If front end processor 102 requires communication with another component such as system controller 114, as is the case in ultrasound information processing system 100 of FIG. 1, a different link 122 is used. Furthermore, the link 118 is custom in that the required terminal units, drivers, and physical layer protocols are specifically chosen or designed (number of bits, speed, timing signals, etc.) for the type of data traffic between the front end processor 102 and the back end processor 104, in particular for high-speed interchange of large multidimensional ultrasound vector data therebetween.

In contrast to the link 118, the link 122 is dedicated between the front end processor 102 and the system controller 114 and is customized for a different purpose. The link 122 is only required to carry control commands between the system controller 114 and the front end processor 102, and therefore the required terminal units, drivers, and physical layer protocols may be chosen or designed for low-speed data throughput.

Disadvantageously, due to the use of custom, dedicated communication links among its components, the ultrasound information processing system 100 is not easily adaptable to different configurations, upgradable to newer, better, and/or less expensive hardware, or changeable to new software ultrasound information processing algorithms. In practice, the architecture of the ultrasound information processing system 100 is implemented by a single manufacturer, who designs a custom backplane into which custom hardware cards are inserted for performing specific functions, and who designs a custom programming environment into which new ultrasound information processing algorithms must be adapted. Any upgrades in hardware and/or software must correspond directly to the hardware specifications in the custom backplane system and/or the custom programming environment.

As an example, where the existing ultrasound information processing system 100 is made by established manufacturer "X", if a new ultrasound hardware company "N" wishes to provide an upgrade to the video controller 108, company "N" must create a communications interface specifically designed for the dedicated, custom link 120. This communications interface will generally not work with systems made by other established manufacturers "Y" or "Z". As another example, if company "N" creates a newer, faster matrix processor for performing the functions of back end processing subsystem 104, company "N" must create a custom hardware board for plugging into the custom backplane of the system of company "X", and again this custom hardware board will generally not work with systems made by manufacturers "Y" or "Z". Thus, according to the prior art architecture of ultrasound information processing system 100, costs of entry into the ultrasound hardware/software field are increased, choice in upgrading existing ultrasound equipment are reduced, and the spread of advances in the ultrasound arts are inhibited.

Accordingly, it would be desirable-to provide an ultrasound information processing architecture that allows for appropriate data communication, including high-speed data communications, among components thereof.

It would be further desirable to provide an ultrasound information processing architecture that allows for flexible, expandable, and adaptable implementation of components from any of a variety of manufacturers.

It would be even further desirable to provide an ultrasound information processing architecture that allows for ready implementation of new software ultrasound information processing algorithms into existing ultrasound hardware or new ultrasound hardware as the situation requires.

It would be even further desirable to provide an ultrasound information processing architecture that standardizes communications among ultrasound hardware and software components, to allow upgrades without substantial change to existing ultrasound equipment investments.

SUMMARY OF THE INVENTION

In accordance with a preferred embodiment, an architecture and protocol are provided for allowing a flexible, low cost, expandable, and upgradable ultrasound information processing system, wherein ultrasound information processing functions are performed by a plurality of ultrasound modules coupled to a high-speed serial ultrasound information bus. The ultrasound information bus is used for packetized data transfer among the ultrasound modules in accordance with an ultrasound information exchange protocol. Additional or upgraded ultrasound modules are designed to connect to the ultrasound information bus and to communicate using the ultrasound information exchange protocol. Thus, according to a preferred embodiment, as improvements in hardware technology or software algorithms are made, additional or upgraded ultrasound modules are simply "plugged in" to the ultrasound information bus, thereby reducing costs and increasing system versatility and upgradability.

In a preferred embodiment, the ultrasound information exchange protocol provides for ultrasound data interchange among ultrasound modules, each of which is given a unique network address. Ultrasound information exchange protocol packets are routed from a source ultrasound module to a destination ultrasound module across the ultrasound information bus. Accordingly, ultrasound information is readily shared by different clinical facilities using the ultrasound information exchange protocol, thereby allowing for accelerated research and development, easy and inexpensive testing of new ultrasound equipment and algorithms, convenient central archiving of ultrasound information data, and other benefits.

In another preferred embodiment, a hospital ultrasound information network is formed by the ultrasound stations modules and the ultrasound information bus at a given clinical site, each ultrasound module being provided with a unique TCP/IP address.

DETAILED DESCRIPTION

Figure 2:
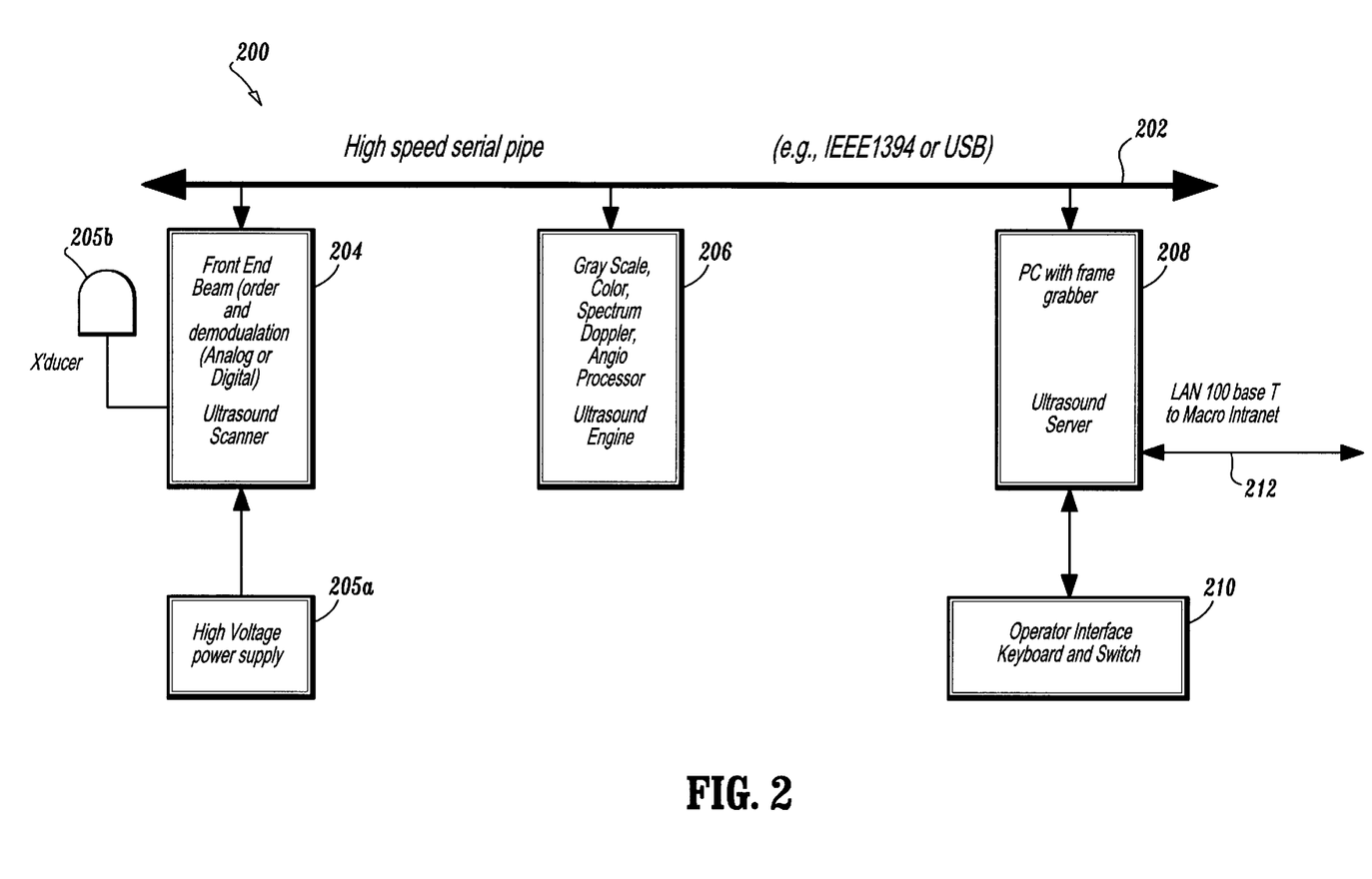
FIG. 2 shows an ultrasound information processing system in accordance with a preferred embodiment.

FIG. 2 shows an ultrasound information processing system 200 in accordance with a preferred embodiment. Ultrasound information processing system 200 comprises an ultrasound information bus 202, an ultrasound scanner 204, an ultrasound engine 206, and an ultrasound server 208. Ultrasound information bus 202 comprises a high-speed, multiple-drop serial bus capable of supporting high bit rate traffic, e.g., 400 Mbps or greater. It has been found that the IEEE 1394 "Firewire" standard or the Fibre Channel standard provides suitable physical and link layer connectivity for supporting high-speed ultrasound data communications, although the scope of the preferred embodiments is not so limited.

Presently, the IEEE 1394 "Firewire" standard provides a hardware and software standard for transporting data at 100, 200, or 400 megabits per second (Mbps). Although hardware for 400 Mbps or greater is generally preferred, ultrasound information busses operating at 100 Mbps or greater is within the scope of the preferred embodiments. IEEE 1394 is particularly suitable for low cost, high speed, and flexible implementations for the ultrasound information bus 202. As described in Sheldon, *The Encyclopedia of Networking*, McGraw-Hill (1997) and references cited therein, the contents of which are hereby incorporated by reference into the present application, the IEEE 1394 bus is physically small (the thin serial cable can replace larger and more expensive interfaces), multiple drop, easy to use (no need for terminators, device IDs, or elaborate setup), hot pluggable (users can add or remove 1394 devices with the bus active), inexpensive (priced for consumer products), has a scalable architecture (may mix 100, 200, and 400 Mbps devices on a bus), has a flexible topology (support of daisy chaining and branching for true peer-to-peer communication), and is high-speed (even multimedia data can be guaranteed its bandwidth for just-in-time delivery).

Advantageously, the IEEE 1394 standard simultaneously supports both asynchronous and isochronous transfer of data. Asynchronous transport, which is a traditional method of transmitting data between computers and peripherals, may be used for transmitting low-speed ultrasound information such as command and signalling data among the ultrasound modules. Isochronous data channels provide guaranteed data transport at a pre-determined rate, which is especially important for time-critical portions of information associated with ultrasound applications, such as video and audio signals and multidimensional vector data associated with ultrasound echo signals.

IEEE 1394 involves the low three ISO protocol layers including the Physical Layer, the Link Layer, and the Transaction Layer, plus a Serial Bus Management process that connects to all three layers. The Physical Layer connects devices to the 1394 connector and the other layers connect to the application. The Physical Layer provides the electrical and mechanical connection between the 1394 device and the 1394 cable. Besides the actual data transmission and reception tasks, the Physical Layer provides arbitration to insure all devices have fair access to the bus. The Link Layer provides data packet delivery service for the two types of packet delivery (asynchronous and isochronous). The Transaction Layer supports the asynchronous protocol write, read, and lock commands. A write sends data from the originator to the receiver and a read returns the data to the originator. Lock combines the function of the write and read commands by producing a round trip routing of data between sender and receiver including processing by the receiver. Serial Bus Management provides overall configuration control of the serial bus in the form of optimizing arbitration timing, guarantee of adequate electrical power for all devices on the bus, assignment of which 1394 device is the cycle master, assignment of isochronous channel ID, and basic notification of errors. Bus management is built upon IEEE 1212 standard register architecture.

To transmit data, an IEEE 1394 device first requests control of the physical layer. With asynchronous transport, the address of both the sender and the receiver is transmitted followed by the actual packet data. Once the receiver accepts the packet, a packet acknowledgment is returned to the original sender. To improve throughput, the sender may continue transmission until 64 transactions are outstanding. If a negative acknowledgment should be returned, error recovery is initiated.

With isochronous transport, the sender requests an isochronous channel with a specific bandwidth. Isochronous channel IDs are transmitted followed by the packet data. The receiver monitors the incoming data's channel ID and accepts only data with the specified ID. In accordance with a preferred embodiment, a higher-layer protocol including an ultrasound information exchange protocol is responsible for determining how many isochronous channels are needed and their required bandwidth. Up to 64 isochronous channels may be defined. The bus is configured to send a start of frame timing indicator in the form of a timing gap. This is followed by the time slots for defined isochronous channels. What time remains may be used for any pending asynchronous transmission. Since the slots for each of the isochronous channels have been established, the bus can guarantee their bandwidth and thus their successful delivery.

Ultrasound scanner 204 provides functionality known in the art including front end beam forming and demodulation. Ultrasound engine 206 provides for high-speed ultrasound data processing known in the art corresponding, for example, to the functions of the front end processing subsystem 102 and back end processing subsystem 104 of FIG. 1, supra. Ultrasound server 208 provides overall system control, video display, and audio output, interfacing with the operator via operator interface 210, and communicating with other computing systems via a LAN interface 212. Although three ultrasound devices 204, 206, and 208 are shown in FIG. 2, it is to be appreciated that there may be many more such ultrasound devices, or as few as two devices, coupled to the ultrasound information bus 202. For example, it is within the scope of the preferred embodiments that ultrasound scanner 204 and ultrasound engine 206 may be combined to share a single interface to the ultrasound information bus 202, or in general for any two or more of the ultrasound devices to be combined to share a single interface to the ultrasound information bus 202.

Figure 3:
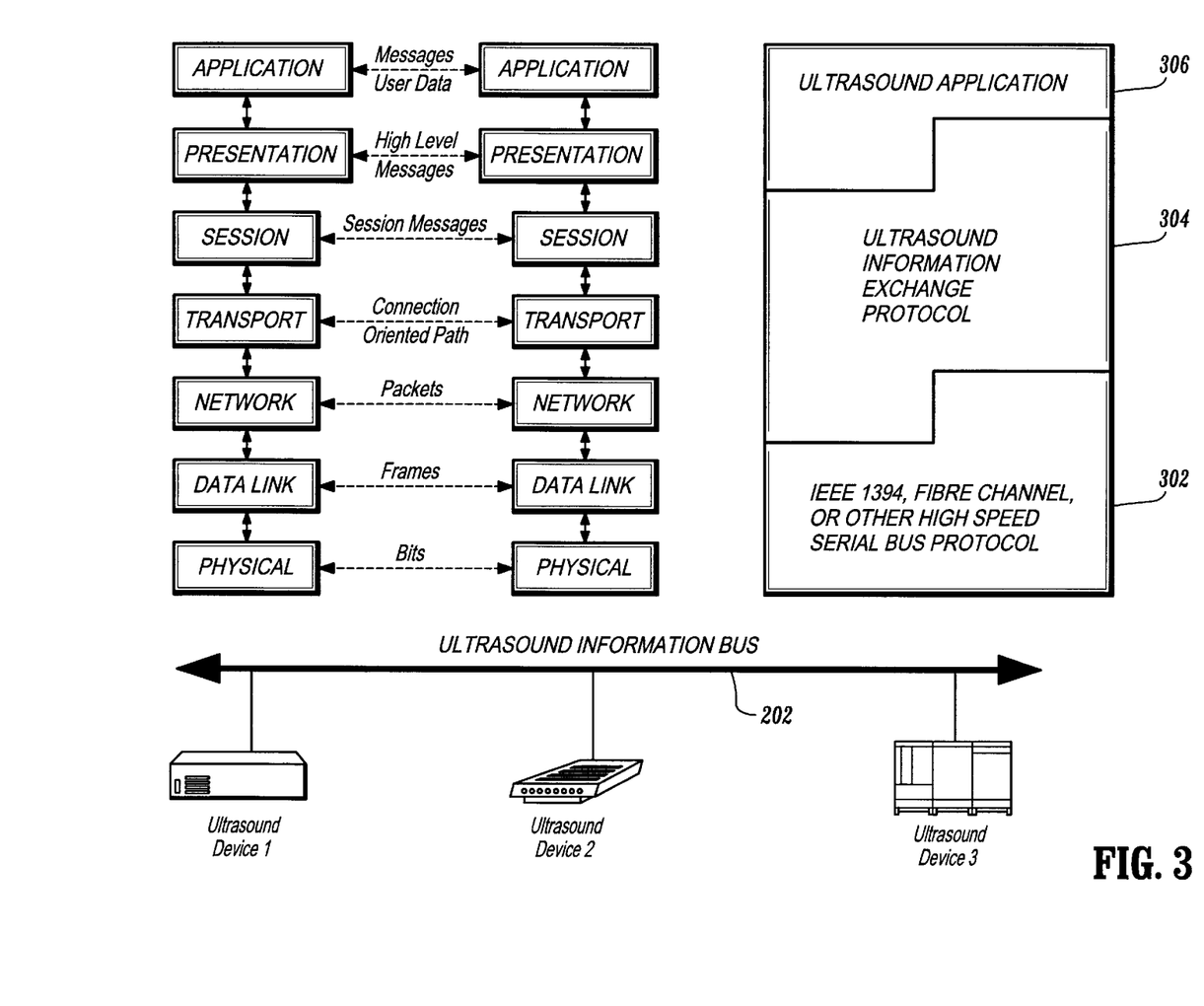
FIG. 3 shows a conceptual diagram communications among ultrasound modules across an ultrasound information bus in accordance with a preferred embodiment.

FIG. 3 shows a conceptual diagram of the coupling of ultrasound modules across the ultrasound information bus 202 in accordance with a preferred embodiment. FIG. 3 shows three generic ultrasound devices coupled to the ultrasound information bus 202. Importantly, in accordance with the serial bus protocols suitable for ultrasound information bus 202, the ultrasound devices may be coupled anywhere along the ultrasound information bus 202. FIG. 3 shows, at the left hand side, the OSI (open system interconnect) hierarchy, while to the right showing the physical and link layers 302, the ultrasound information exchange protocol layers 304, and the ultrasound application layer 306 in accordance with a preferred embodiment.

As described supra, the physical and link layers and portions of higher layers correspond to the IEEE 1394 protocol or serial bus protocol that provides for high speed connections and guaranteed bandwidth for time-sensitive data (e.g., Fibre Channel). In accordance with a preferred embodiment, an ultrasound information exchange protocol layer 304 is provided that is particularly suited for ultrasound control signals and data, wherein high-level application commands and data are received by the ultrasound information exchange protocol layer 304, seamlessly processed and encapsulated into packets and/or frames required by the serial bus physical/link layers 302, and transmitted across the ultrasound information bus 202 to the appropriate ultrasound destination device. The ultrasound information exchange protocol includes features for sending command and control data over the asynchronous channels of the IEEE 1394 protocol, and includes features for ensuring that time-sensitive video, audio, or multidimensional ultrasound vector data are sent over the isochronous channels. It is to be appreciated, however, that although it is preferable to send the time-sensitive video, audio, or multidimensional ultrasound vector data over the isochronous channels, it is within the scope of the preferred embodiments to send such data over the asynchronous channels as well.

The high-level application commands and data used by the ultrasound application software layer 306 are in the form of a clinical procedure specific ultrasound information processing language, which is.a set of scripts that may be in binary or text format. The following is an example of the ultrasound information processing language for starting the B-mode scan:

command: start B-mode image number of parameters: n number of vectors: 256 number of transmit zones: 4 number of receive zones: 16 start of transmit zone: 2 image depth: 30 cm transmit power: −2 dB vector start time: 20 us and (n−7) parameters.

In accordance with a preferred embodiment, when a new hardware component is created in one of the ultrasound devices, which requires the sequence of packet data to be redesigned, then a new ultrasound information exchange protocol layer 304 software is created. This layer can be implemented in the form of DLL files in the case of Windows NT environments by just simply replacing the software library without changing any part of ultrasound application layer 306.

Figure 4:
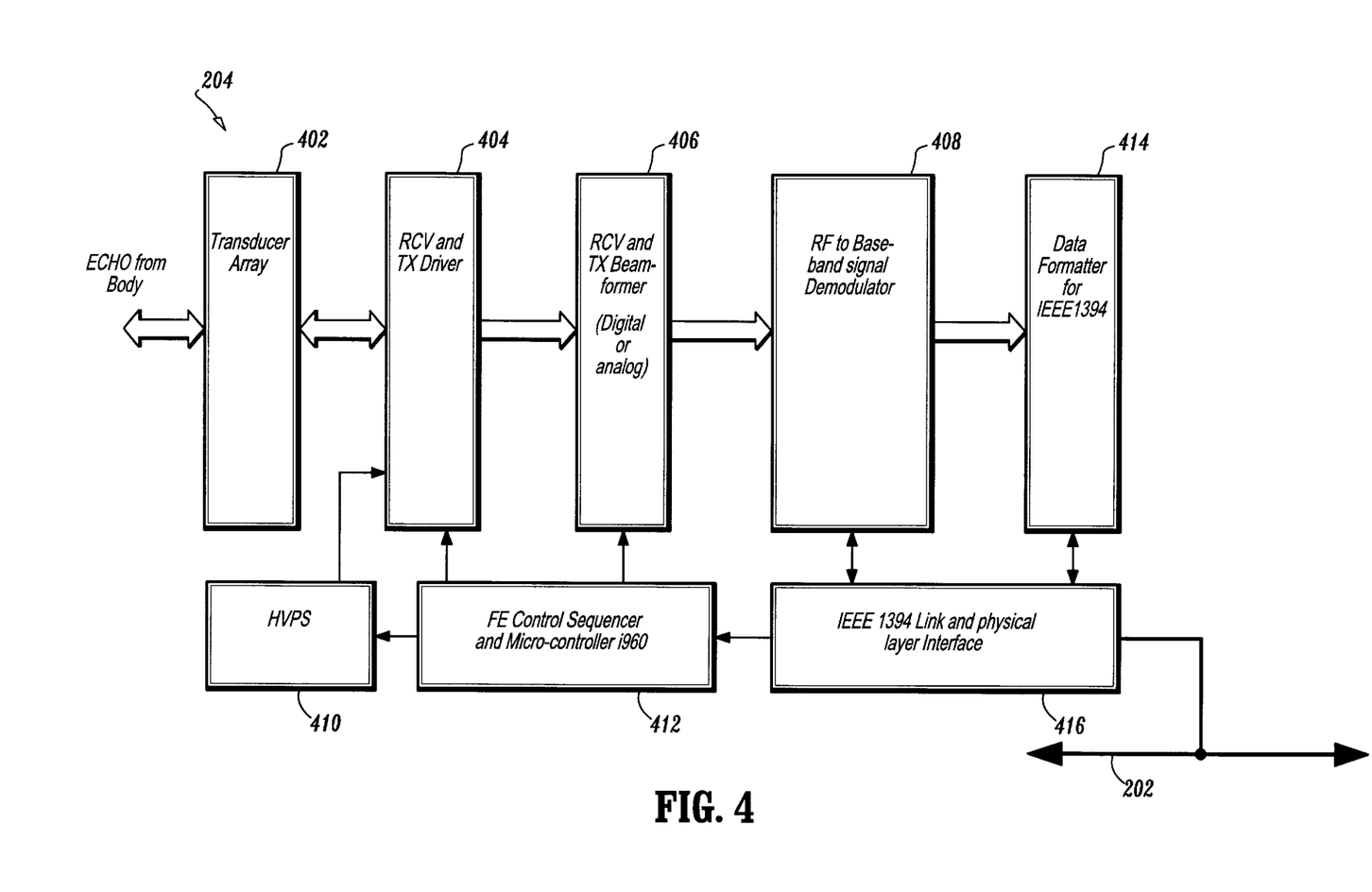
FIG. 4 shows a block diagram of an ultrasound scanner in accordance with a preferred embodiment.

FIG. 4 shows a block diagram of ultrasound scanner 204 in accordance with a preferred embodiment. Ultrasound scanner 204 comprises a transducer array 402, a receive and transmit driver 404, a beamformer 406, an RF to baseband signal demodulator 408, an HV PS unit 410, and a front end control sequencer and microcontroller 412, whose functionality is generally known in the art. Ultrasound scanner 204 further comprises a data formatter 414 for formatting data for IEEE 1394 transmission, the data formatter capable of decoding ultrasound information exchange protocol 304 commands where necessary. Ultrasound scanner 204 further comprises an IEEE 1394 link and physical layer interface 416, preferably designed for 400 Mbps transmission or higher. In a known link and physical layer interface 416 provided by Texas Instruments, three different data speeds of 98.304 Mbps, 196.608 Mbps, and 393.216 Mbps are available. However, expansion to 800 Mbps, 1.6 Gbps, and other or higher speeds is within the scope of the preferred embodiments.

Figure 5:
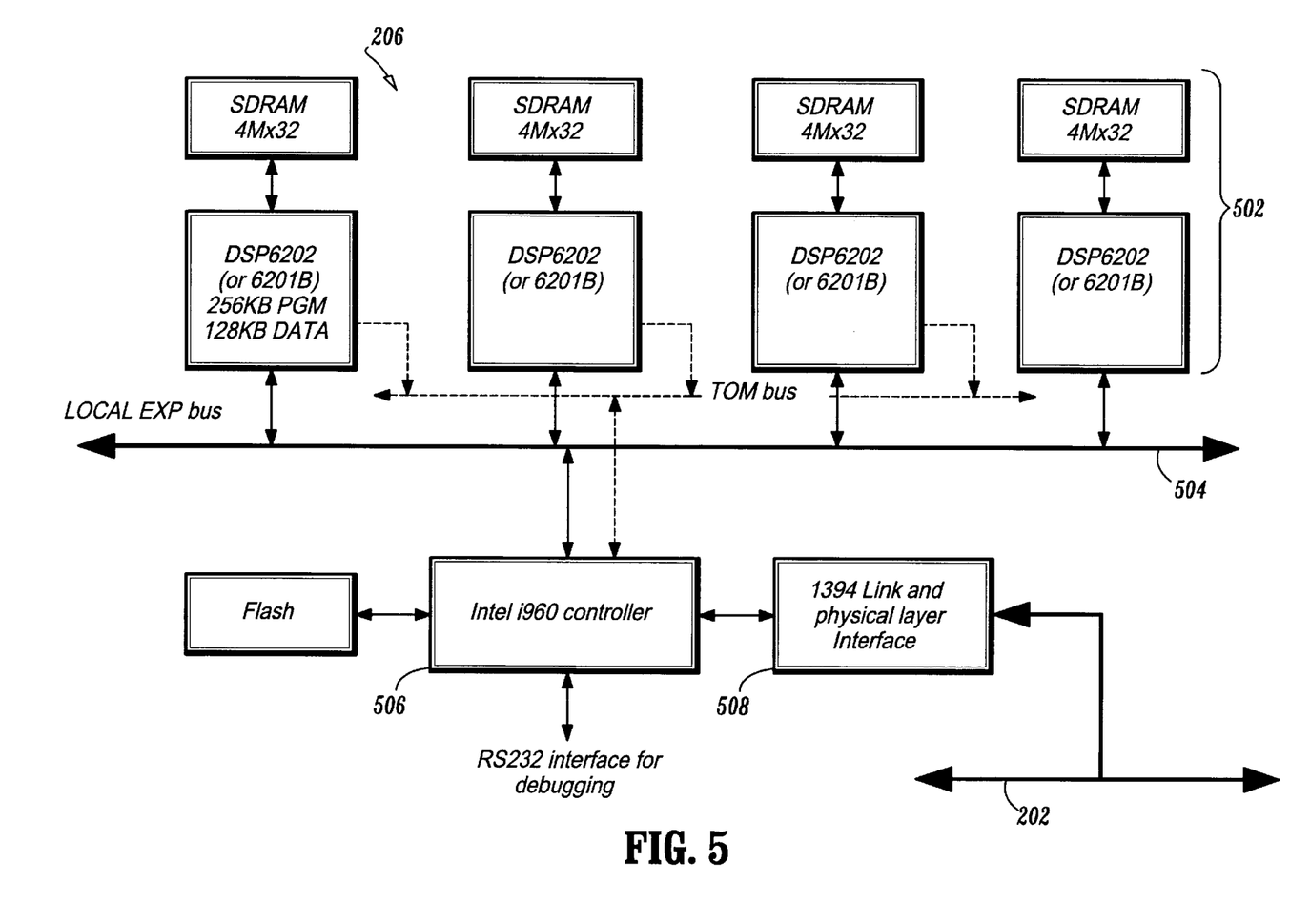
FIG. 5 shows a block diagram of ultrasound engine in accordance with a preferred embodiment.

FIG. 5 shows a block diagram of ultrasound engine 206 in accordance with a preferred embodiment. Ultrasound engine 206 comprises DSP and memory hardware 502, a local EXP bus 504, a controller 506 and an IEEE 1394 link and physical layer interface 508. DSP and memory hardware 502 comprise DSP6202 or 6201B DSP or equivalent processors and 4M×32 SDRAM modules. the DSP units being connected by TDM busses, although it is to be understood that other implementations are within the scope of the preferred embodiments. According to a preferred embodiment, the DSP units are large enough with respect to the ultrasound matrix data such that large data transfers between DSP units over the local EXP bus 504 are avoided, thus increasing system speed. The controller 506 is preferably a flash-programmable Intel i960 or equivalent controller. The IEEE 1394 link and physical layer interface 508 is similar to the IEEE 1394 link and physical layer interface 416, supra. It is to be appreciated that other hardware configurations are within the scope of the preferred embodiments, even to the extent that all functions may be integrated onto a single motherboard or chip, assuming that fast enough hardware may be achieved.

Figure 6:
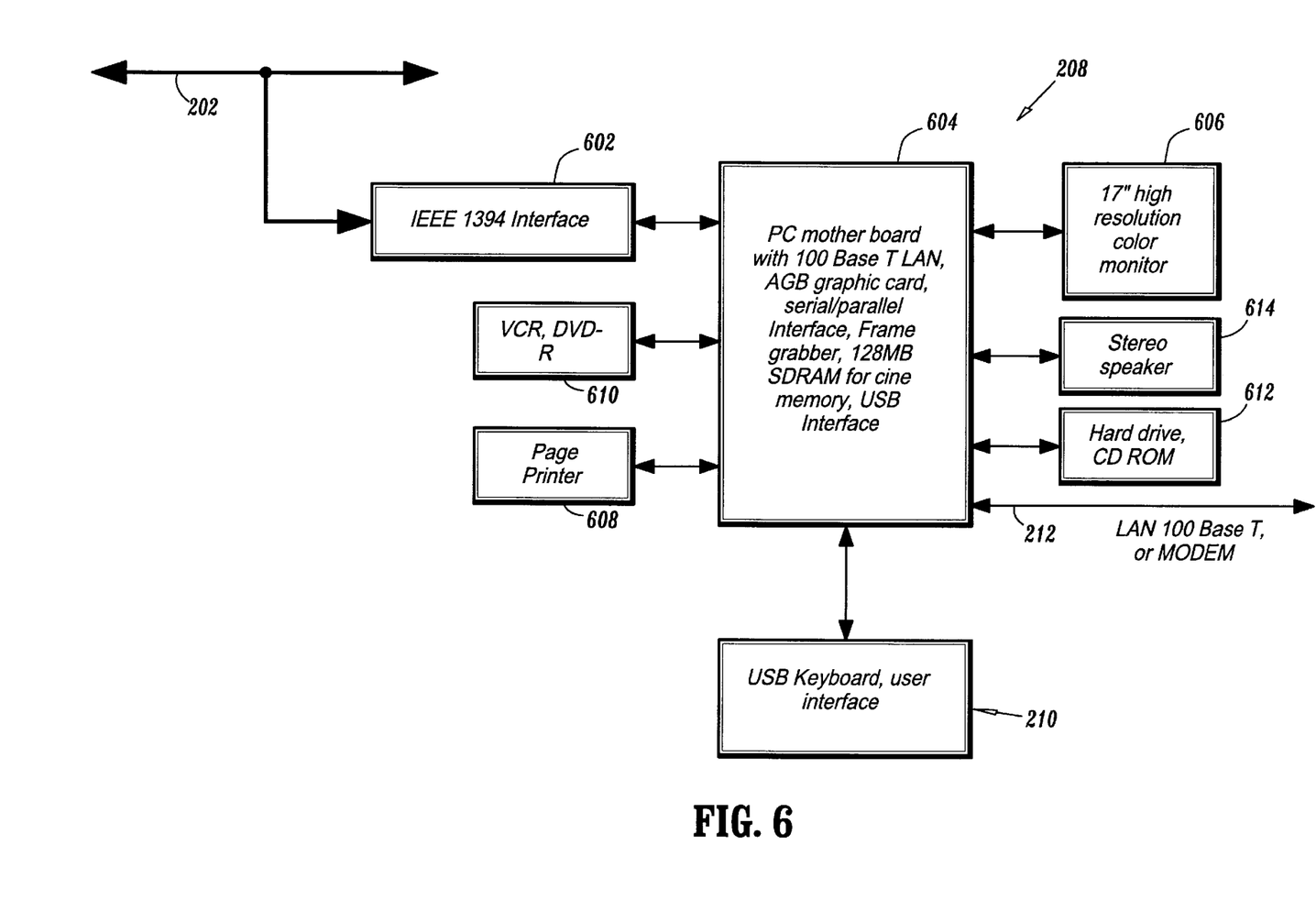
FIG. 6 shows a block diagram of ultrasound server in accordance with a preferred embodiment.

FIG. 6 shows a block diagram of ultrasound server 208 in accordance with a preferred embodiment. The ultrasound server 208 is preferably built using off the shelf hardware components for lower cost. Ultrasound server 208 comprises am IEEE 1394 link and physical layer interface 602, a motherboard 604, a video display 606, and other components similar to those available on PC systems such as a printer or page printer 608, a video device 610, a storage device 612, and an audio output device 614. Ultrasound server 208 is coupled to outside networks using interface 212, which may be a 100BaseT Ethernet interface, a modem, or other communications interface. It is generally not required that the interface 212 to outside networks support isochronous data transfer, although the scope of the preferred embodiments extends to high-speed isochronous data transfer with distant ultrasound devices as necessary, whereby the ultrasound information processing system 200 may be coupled in real-time to other ultrasound information processing systems.

Certain models of peripheral devices such as page printer 608 and video device 610 are already commercially available with IEEE 1394 interface and therefore may be directly plugged in to the ultrasound information bus 202 for communicating with the ultrasound devices attached thereto. As other peripheral display and recording devices with similar interface become commercially available, these devices could also be plugged in to the ultrasound information bus 202. This convenient expandability and flexibility, analogous to a "plug and play" feature, is advantageously provided in accordance with the preferred embodiments.

Figure 7:
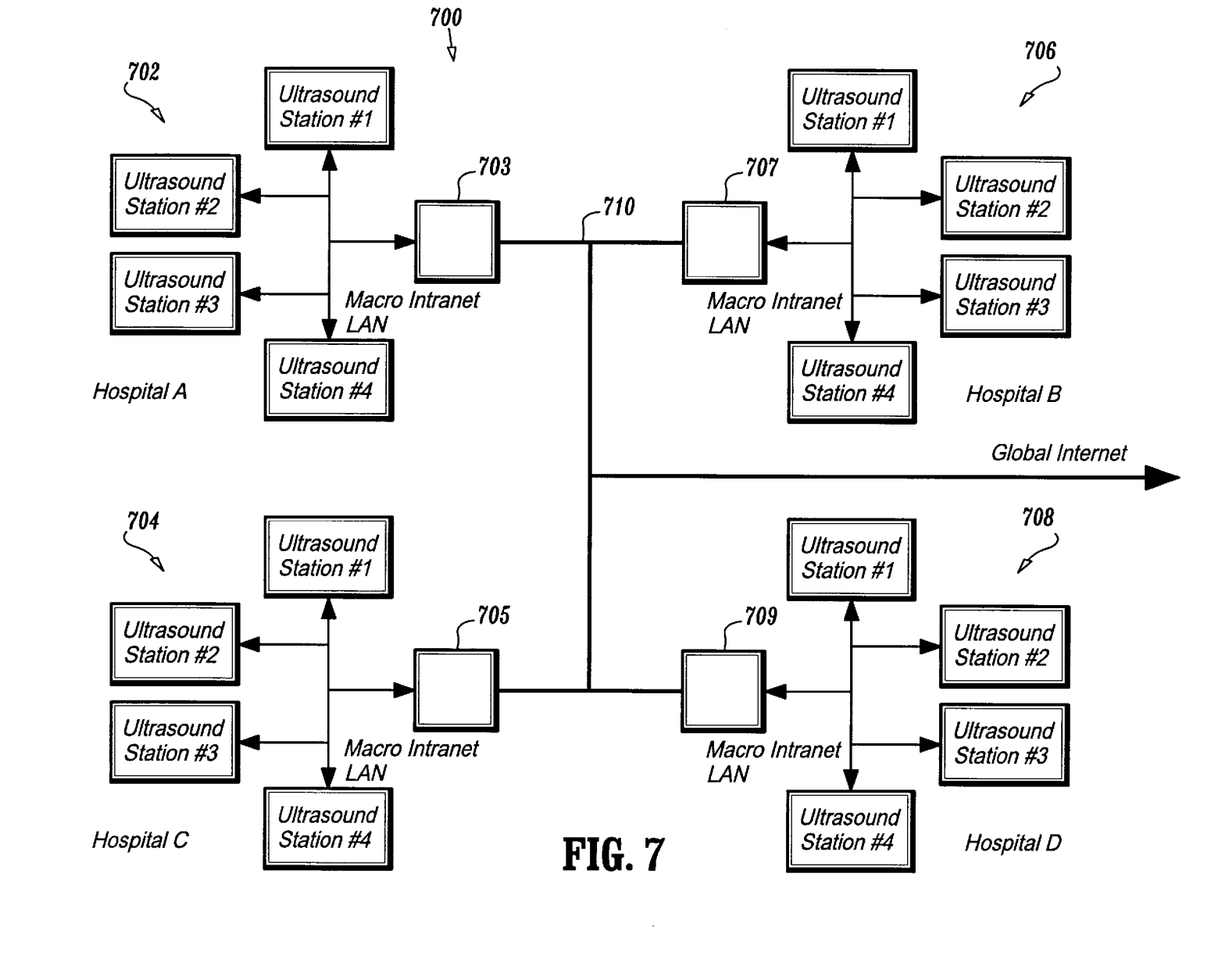
FIG. 7 shows an ultrasound information network in accordance with a preferred embodiment.

FIG. 7 shows an ultrasound information network 700 in accordance with a preferred embodiment. Ultrasound information network 700 comprises a plurality of intranets 702, 704, 706, and 708, each intranet generally corresponding to a plurality of ultrasound information processing systems (labeled as "Ultrasound Stations" in FIG. 7) coupled to a local area network bus such as an Ethernet bus. devices coupled to an ultrasound information bus as described with respect to FIG. 2. Thus, the ultrasound information processing system of FIG. 2 may be considered as one portion of a larger network of ultrasound information devices. Further, each of the intranets 702, 704, 706, and 708 is provided with a hospital information network server 703, 705, 707, and 709, respectively for coupling to a larger hospital network bus 710, which may in turn be coupled to the global Internet. Ultrasound modules on each intranet may be given unique IP addresses for providing flexible data communications among the nodes.

The ultrasound information network 700 may be advantageously used by related clinical sites (e.g. Hospital A, Hospital B, Hospital C, and Hospital D) in accordance with the preferred embodiments. For example, ultrasound displays may be shown to a specialist at Hospital A while the patient is at Hospital B, with voice communications also taking place over data channels on hospital network bus 710. Ultrasound information network 700 may still be used for other purposes such as for collecting ultrasound information for archiving purposes, for analyzing changes in ultrasound characteristics of a given patient over time, for collecting ultrasound statistics, and for providing evidentiary archives for insurance purposes. Generally speaking, communications across the global Internet may serve purposes analogous to those listed above for data transfer among the ultrasound modules.

Figure 8:
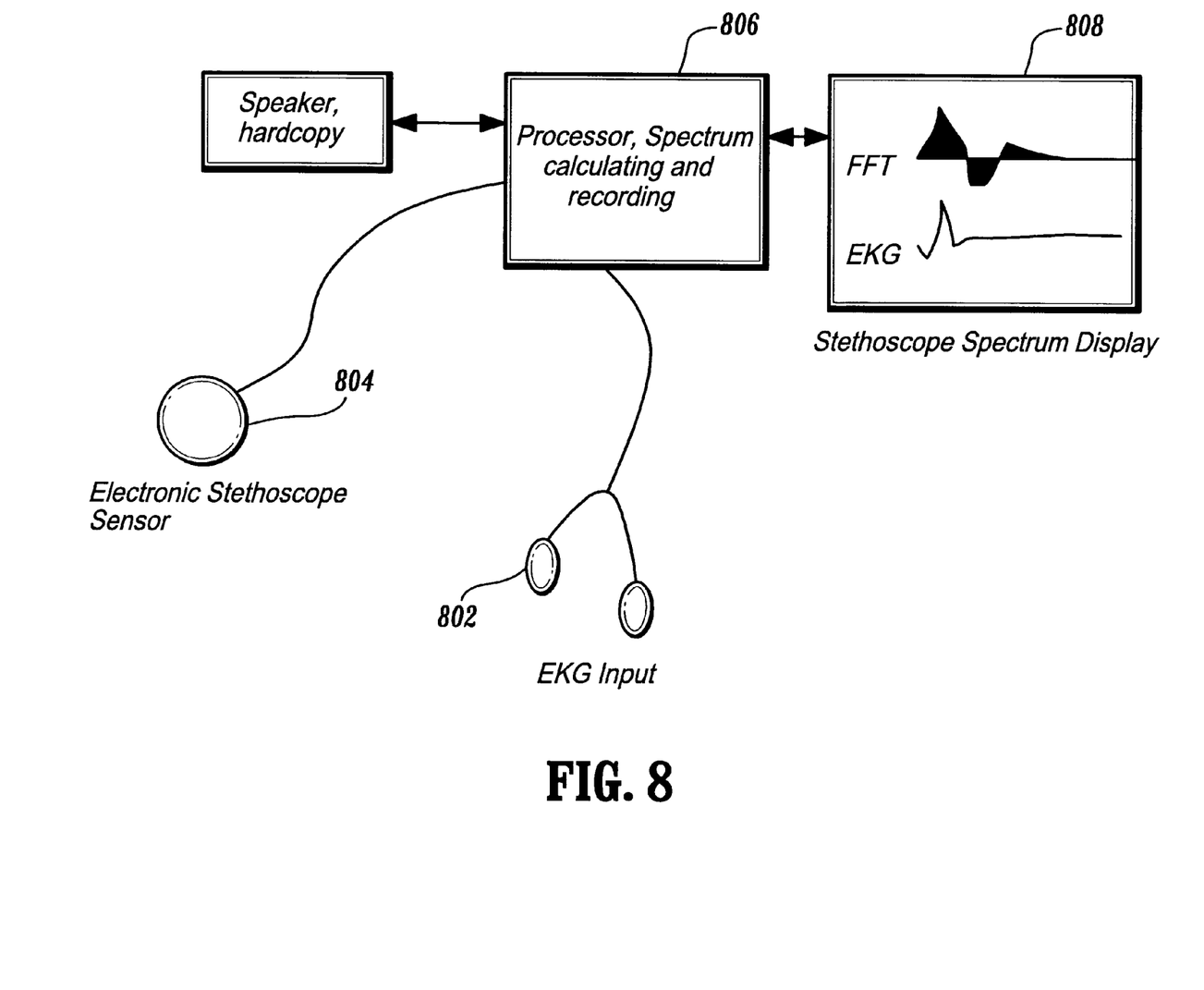
FIG. 8 shows a system for visual display of a stethoscope signal in accordance with a preferred embodiment.

FIG. 8 shows a system for visual display of stethoscope signal characteristics in accordance with a preferred embodiment. In accordance with the prior art, in cases where a patient has a heart or vascular problem, an audio signal from a stethoscope is monitored by a trained medical professional who can detect irregularities (e.g., clicks associated with heart murmurs) with their ear. However, a problem may arise if a medical professional's hearing deteriorates over time, or the medical professional is otherwise insensitive to subtle audio variations. It is therefore desirable to provide a method of evaluating stethoscope audio signals that does not rely exclusively on the human ear.

Accordingly, FIG. 8 shows a method for using an EKG Input 802 signal in conjunction with an electronic stethoscope sensor input 804 at a processor 806 to produce a visual display 808 that provides visual information related to the stethoscope signal. In particular, in accordance with a preferred embodiment, processor 806 uses regular heartbeat intervals provided by the R-wave of the EKG Input 802 to window the audio signals from the stethoscope input 804. Each windowed audio signal, having a duration corresponding to the period of the patient's heartbeat (or predetermined fraction or multiple thereof), is fed to a one-dimensional spectrum analyzer which computes the Fourier Transform of the windowed signal. The Fourier transform (or, more particularly, the Fast Fourier Transform or FFT) is then displayed to the medical professional. It has been found that using the EKG signal to provide window or trigger for the one-dimensional FFT of a stethoscope signal as described above can provide a useful, quantitative display of stethoscope signals. Audio stethoscope signals may be verified by visual examination of the display 808, which may reveal irregularities not audible to the human ear or, more particularly, to the human ear of a given medical professional on a given day. Scientific analysis techniques, such as data sample gathering, clinical studies, and the like may be performed to identify "normal" FFT signatures versus "pathological" FFT signatures for population samples of patients. Advantageously, it has been found that the ultrasound information processing system 200 may be readily modified to perform the above functions. As known in the art, most ultrasound systems already comprise an EKG input (for strobing the ultrasound image of the heart at a particular point in the heartbeat cycle), a video display, and high speed hardware capable of fast computation of FFT's. Accordingly, with the relatively simple addition of an electronic stethoscope input, the ultrasound information processing system 200 is readily adaptable for providing the windowing, FFT, and visual display of audio stethoscope signals according to the embodiment of FIG. 8.

While certain preferred embodiments have been described, these descriptions are merely illustrative and are not intended to limit the scope of the preferred embodiments. For example, within the scope of the preferred embodiments is a distributed ultrasound information processing system having components at several different sites that are coupled by an ultrasound information network. The ultrasound information network may allow the processing services of centralized ultrasound modules to be shared by different remote ultrasound installations coupled thereto via high-speed isochronous data channels. Indeed, within the scope of the preferred embodiments is an ultrasound network wherein remote ultrasound systems only have "dumb" front end (scanner) and back end (display) equipment, wherein the required ultrasound computations are performed by a centralized ultrasound server which is offered on a per-use or a subscription basis.

What is claimed is:

1. An ultrasound information processing system, comprising:
    a first internal ultrasound processing device for performing a first internal ultrasound processing function;
    a second internal ultrasound processing device for performing a second internal ultrasound processing function, said second internal ultrasound processing function using data derived from said first internal ultrasound function, said first and second internal ultrasound processing functions each corresponding to one or more steps taken in the real-time conversion of acoustic scan signal data into viewable image data; and
    an ultrasound information bus coupled to said first internal ultrasound processing device and said second internal ultrasound processing device, said ultrasound information bus operating according to a high-speed packetized serial bus protocol providing at least one isochronous channel for transferring real-time data associated with said real-time conversion and at least one asynchronous channel for transferring command or signaling data associated with said real-time conversion.

2. The ultrasound information processing system of claim 1, further comprising a third ultrasound processing device coupled to said ultrasound information bus, said third ultrasound processing device for performing a third ultrasound processing function, said third ultrasound processing function using data derived from said first and second ultrasound processing functions.

3. The ultrasound information processing system of claim 2, said third ultrasound processing device being programmed in accordance with an ultrasound protocol stack, said ultrasound protocol stack comprising:
    a physical and data link layer corresponding to a high-speed serial bus protocol;
    an ultrasound information exchange protocol layer; and
    an ultrasound applications programming layer;
    wherein additional ultrasound processing devices may be designed for said ultrasound information processing system in a modular fashion by custom-programming said ultrasound applications programming layer, and providing pre-designed modules according to said ultrasound information exchange protocol layer and said physical and data link layer.

4. The ultrasound information processing system of claim 3, said additional ultrasound devices being provided with a front end standardized with said high-speed serial bus protocol, wherein said additional devices may be added to said ultrasound information processing system without requiring hardware reconfiguration of said first, second, or third ultrasound processing devices.

5. The ultrasound information processing system of claim 4, wherein said high-speed serial bus protocol is an IEEE 1394 compatible protocol operating at 100 Mbps or greater.

6. The ultrasound information processing system of claim 4, wherein said high-speed serial bus protocol is a Fibre Channel compatible protocol operating at 100 Mbps or greater.

7. An ultrasound information processing system, comprising:
    an ultrasound scanning module for receiving ultrasound echo signals in real time and producing therefrom a first intermediate result;
    an ultrasound engine for processing in real time said first intermediate result to produce a second intermediate result;
    an ultrasound server for providing control signals to said ultrasound scanning module and said ultrasound engine and for providing a real-time visual display of a viewable output image generated from said second intermediate result; and
    an ultrasound information bus coupled to said ultrasound scanning module, said ultrasound engine, and said ultrasound information bus operating according to a high-speed serial bus protocol providing a first isochronous channel for transferring said first intermediate result from said ultrasound scanning module to said ultrasound engine, a second isochronous channel for transferring said second intermediate result from said ultrasound engine to said ultrasound server, and at least one asynchronous channel for transferring said control signals from said ultrasound server to said ultrasound scanning module and said ultrasound engine.

8. The ultrasound information processing system of claim 7, said ultrasound server being programmed in accordance with an ultrasound protocol stack, said ultrasound protocol stack comprising:
    a physical and data link layer corresponding to a high-speed serial bus protocol;
    an ultrasound information exchange protocol layer; and
    an ultrasound applications programming layer;
    wherein additional ultrasound processing devices may be designed for said ultrasound information processing system in a modular fashion by custom-programming said ultrasound applications programming layer, and providing pre-designed modules according to said ultrasound information exchange protocol layer and said physical and data link layer.

9. The ultrasound information processing system of claim 8, said additional ultrasound devices being provided with a front end standardized with said high-speed serial bus protocol, wherein said additional devices may be added to said ultrasound information processing system without requiring hardware reconfiguration of said ultrasound scanning module, said ultrasound engine, or said ultrasound server.

10. The ultrasound information processing system of claim 9, wherein said high-speed serial bus protocol is an IEEE 1394 compatible protocol operating at 100 Mbps or greater.

11. The ultrasound information processing system of claim 9, wherein said high-speed serial bus protocol is a Fibre Channel compatible protocol operating at 100 Mbps or greater.

12. An ultrasound imaging system capable of real-time processing of acoustic interrogation echo signals into a viewable image format, comprising:

- a first ultrasound processing device for performing a first ultrasound processing function, said first ultrasound processing device being internal to the ultrasound imaging system;
- a second internal ultrasound processing device for performing a second ultrasound processing function, said second ultrasound processing function using data derived from said first ultrasound function, said second ultrasound processing device being internal to the ultrasound imaging system, said first and second ultrasound processing functions each corresponding to one or more steps taken in said real-time processing of said acoustic interrogation signals into said viewable image format; and
- an ultrasound information bus coupled to said first ultrasound processing device and said second ultrasound processing device, said ultrasound information bus operating according to a high-speed packetized serial bus protocol providing at least one isochronous channel for transferring real-time data associated with said real-time processing and at least one asynchronous channel for transferring command or signaling data associated with said real-time processing.

13. The ultrasound imaging system of claim 12, further comprising a third ultrasound processing device coupled to said ultrasound information bus, said third ultrasound processing device for performing a third ultrasound processing function, said third ultrasound processing function using data derived from said first and second ultrasound processing functions, said third ultrasound processing device being internal to the ultrasound imaging system, wherein said high-speed serial bus protocol provides for isochronous data transfer.

14. The ultrasound imaging system of claim 13, said third ultrasound processing device being programmed in accordance with an ultrasound protocol stack, said ultrasound protocol stack comprising:

- a physical and data link layer corresponding to a high-speed serial bus protocol:
- an ultrasound information exchange protocol layer; and
- an ultrasound applications programming layer;
- wherein additional ultrasound processing devices may be designed for said ultrasound information processing system in a modular fashion by custom-programming said ultrasound applications programming layer, and providing pre-designed modules according to said ultrasound information exchange protocol layer and said physical and data link layer.

15. The ultrasound imaging system of claim 14, said additional ultrasound devices being provided with a front end standardized with said high-speed serial bus protocol, wherein said additional devices may be added to said ultrasound information processing system without requiring hardware reconfiguration of said first, second, or third ultrasound processing devices.

16. The ultrasound imaging system of claim 15, wherein said high-speed serial bus protocol is an IEEE 1394 compatible protocol operating at 100 Mbps or greater.

17. The ultrasound imaging system of claim 15, wherein said high-speed serial bus protocol is a Fibre Channel compatible protocol operating at 100 Mbps or greater.

18. The ultrasound imaging system of claim 15, wherein said high-speed serial bus protocol is a Universal Serial Bus (USB) compatible protocol.

19. The ultrasound imaging system of claim 18, wherein said first ultrasound processing device comprises an ultrasound probe for generating acoustic interrogation signals and receiving acoustic interrogation echo signals, and wherein said second ultrasound processing device comprises an ultrasound engine for processing information derived from said acoustic interrogation echo signals.

\* \* \* \* \*